United States Patent
Shiu et al.

(10) Patent No.: US 9,867,664 B2
(45) Date of Patent: Jan. 16, 2018

(54) SYSTEM AND METHOD OF DEPLOYING AN ANTENNA ASSEMBLY

(75) Inventors: Brian Shiu, Sunnyvale, CA (US); Kyle R. Rick, Boulder, CO (US); Mani N. Prakash, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1836 days.

(21) Appl. No.: 12/772,675

(22) Filed: May 3, 2010

(65) Prior Publication Data

US 2011/0270240 A1 Nov. 3, 2011

(51) Int. Cl.
*A61B 18/18* (2006.01)

(52) U.S. Cl.
CPC .. *A61B 18/1815* (2013.01); *A61B 2018/1838* (2013.01); *A61B 2018/1853* (2013.01); *A61B 2018/1869* (2013.01)

(58) Field of Classification Search
CPC ........ A61B 18/1815; A61B 2018/0091; A61B 2018/0094; A61B 2018/00946; A61B 2018/00952; A61B 2018/1475; A61B 2018/1838; A61B 2018/1869
USPC .......................... 606/32–33, 41; 607/98–103
See application file for complete search history.

(56) References Cited

U.S. PATENT DOCUMENTS

| | | |
|---|---|---|
| D263,020 S | 2/1982 | Rau, III |
| 4,616,656 A | 10/1986 | Nicholson et al. |
| D295,893 S | 5/1988 | Sharkany et al. |
| D295,894 S | 5/1988 | Sharkany et al. |
| 5,441,483 A * | 8/1995 | Avitall ....................... 604/95.05 |
| 5,545,200 A * | 8/1996 | West et al. ..................... 607/122 |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D496,997 S | 10/2004 | Dycus et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Michael Peffley
*Assistant Examiner* — Samantha Good

(57) ABSTRACT

A method of deploying an antenna of an ablation device includes the step of placing an introducing member relative to tissue. The introducing member is disposed on a distal end of a handle member. The method also includes the steps of advancing an antenna distally through the handle member and at least partially through the introducer and rotating the handle member about the longitudinal axis thereof relative to the antenna. The method also includes the step of moving the handle member proximally along the longitudinal axis thereof to retract the introducer proximally relative to the antenna such that the antenna is at least partially deployed relative to the introducer to treat tissue.

9 Claims, 10 Drawing Sheets

(56) References Cited

U.S. PATENT DOCUMENTS

| | | | |
|---|---|---|---|
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,282,020 B2 | 10/2007 | Kaplan | |
| D564,662 S | 3/2008 | Moses et al. | |
| D613,412 S | 4/2010 | DeCarlo | |
| 2004/0030334 A1* | 2/2004 | Quick et al. | 606/45 |
| 2009/0248006 A1 | 10/2009 | Paulus et al. | |
| 2010/0160911 A1* | 6/2010 | Ducharme | 606/46 |
| 2011/0152923 A1* | 6/2011 | Fox | A61B 17/0057 606/213 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO2010/035831 | 9/2009 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.

(56) References Cited

OTHER PUBLICATIONS

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-lridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakcami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.

(56) References Cited

OTHER PUBLICATIONS

Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.

(56) References Cited

OTHER PUBLICATIONS

European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 12/389,906, filed Feb. 20, 2009, Francesca Rossetto.
U.S. Appl. No. 12/389,915, filed Feb. 20, 2009, Francesca Rossetto.
U.S. Appl. No. 12/401,268, filed Mar. 10, 2009, Ian Smith.
U.S. Appl. No. 12/416,583, filed Apr. 1, 2009, Joseph D. Brannan.
U.S. Appl. No. 12/423,609, filed Apr. 14, 2009, Jeffrey L. Jensen.
U.S. Appl. No. 12/436,231, filed May 6, 2009, Ronald J. Podhajsky.
U.S. Appl. No. 12/436,237, filed May 6, 2009, Ronald J. Podhajsky.
U.S. Appl. No. 12/436,239, filed May 6, 2009, Ronald J. Podhajsky.
U.S. Appl. No. 12/472,831, filed May 27, 2009, Joseph D. Brannan.
U.S. Appl. No. 12/475,082, filed May 29, 2009, Darion Peterson.
U.S. Appl. No. 12/476,960, filed Jun. 2, 2009, Mani N. Prakash.
U.S. Appl. No. 12/487,917, filed Jun. 19, 2009, Joseph D. Brannan.
U.S. Appl. No. 12/493,302, filed Jun. 29, 2009, Darion Peterson.
U.S. Appl. No. 12/504,738, filed Jul. 17, 2009, Robert J. Behnke.
U.S. Appl. No. 12/535,851, filed Aug. 5, 2009, Joseph D. Brannan.
U.S. Appl. No. 12/535,856, filed Aug. 5, 2009, Joseph D. Brannan.
U.S. Appl. No. 12/536,616, filed Aug. 6, 2009, Arnold V. DeCarlo.
U.S. Appl. No. 12/542,348, filed Aug. 17, 2009, Joseph D. Brannan.
U.S. Appl. No. 12/542,785, filed Aug. 18, 2009, Joseph D. Brannan.
U.S. Appl. No. 12/547,155, filed Aug. 25, 2009, Robert J. Behnke.
U.S. Appl. No. 12/548,644, filed Aug. 27, 2009, Darion Peterson.
U.S. Appl. No. 12/555,576, filed Sep. 8, 2009, Kenlyn S. Bonn.
U.S. Appl. No. 12/556,010, filed Sep. 9, 2009, Ian S. Smith.
U.S. Appl. No. 12/556,238, filed Sep. 9, 2009, Kenlyn S. Bonn.
U.S. Appl. No. 12/561,096, filed Sep. 16, 2009, Kenlyn S. Bonn.
U.S. Appl. No. 12/562,575, filed Sep. 18, 2009, Joseph D. Brannan.
U.S. Appl. No. 12/562,842, filed Sep. 18, 2009, Robert J. Behnke.
U.S. Appl. No. 12/566,299, filed Sep. 24, 2009, Richard A. Willyard.
U.S. Appl. No. 12/568,067, filed Sep. 28, 2009, Francesca Rossetto.
U.S. Appl. No. 12/568,524, filed Sep. 28, 2009, Kenlyn S. Bonn.
U.S. Appl. No. 12/568,551, filed Sep. 28, 2009, Joseph D. Brannan.
U.S. Appl. No. 12/568,777, filed Sep. 29, 2009, Kenlyn S. Bonn.
U.S. Appl. No. 12/568,838, filed Sep. 29, 2009, Kenlyn S. Bonn.
U.S. Appl. No. 12/568,883, filed Sep. 29, 2009, Joseph D. Brannan.
U.S. Appl. No. 12/568,972, filed Sep. 29, 2009, Joseph D. Brannan.
U.S. Appl. No. 12/569,171, filed Sep. 29, 2009, Joseph D. Brannan.
U.S. Appl. No. 12/569,685, filed Sep. 29, 2009, Joseph D. Brannan.
U.S. Appl. No. 12/582,857, filed Oct. 21, 2009, Charles D. Allen.
U.S. Appl. No. 12/606,769, filed Oct. 27, 2009, Joseph D. Brannan.
U.S. Appl. No. 12/607,221, filed Oct. 28, 2009, Joseph D. Brannan.
U.S. Appl. No. 12/607,268, filed Oct. 28, 2009, Joseph D. Brannan.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.

(56) References Cited

OTHER PUBLICATIONS

U.S. Appl. No. 12/732,521, filed Mar. 26, 2010, Steven Kim.
U.S. Appl. No. 12/761,267, filed Apr. 15, 2010, Jonathan A. Coe.
U.S. Appl. No. 12/769,457, filed Apr. 28, 2010, Gene H. Arts.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakas.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/819,330, filed Jun. 21, 2010, Jonathan A. Co.
U.S. Appl. No. 12/823,211, filed Jun. 25, 2010, Mani N. Prakash.
U.S. Appl. No. 12/826,902, filed Jun. 30, 2010, Brian Shiu.
U.S. Appl. No. 08/136,098, filed Oct. 14, 1993, Roger A. Stern.
U.S. Appl. No. 08/483,742, filed Jun. 7, 1995, Roger A. Stern.

\* cited by examiner

SYSTEM AND METHOD OF DEPLOYING AN ANTENNA ASSEMBLY

BACKGROUND

1. Technical Field

The present disclosure relates to ablation devices and methods. More particularly, the disclosure relates to systems and methods for deploying an ablation antenna assembly into tissue.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

SUMMARY

According to an embodiment of the present disclosure, a method of deploying an antenna of an ablation device includes the step of placing an introducing member relative to tissue. The introducing member is disposed on a distal end of a handle member. The method also includes the steps of advancing an antenna distally through the handle member and at least partially through the introducer and rotating the handle member about the longitudinal axis thereof relative to the antenna. The method also includes the step of moving the handle member proximally along the longitudinal axis thereof to retract the introducer proximally relative to the antenna such that the antenna is at least partially deployed relative to the introducer to treat tissue.

According to another embodiment of the present disclosure, an antenna assembly includes a handle member defining a longitudinal axis and having a feedline disposed on its distal end. The feedline extends along the longitudinal axis and includes an inner conductor disposed within an outer conductor. The inner conductor is deployable relative to the outer conductor and configured to deliver energy from an energy source to tissue. The antenna assembly also includes a first track portion disposed longitudinally along at least a portion of the handle member. The first track portion has a distal end intersecting a second track portion disposed perpendicular to the first track portion and latitudinal along at least a portion of the handle member. The second track portion intersects a proximal end of a third track portion disposed longitudinally along at least a portion of the handle member. The antenna assembly also includes an actuating member movable longitudinally within the first and third track portions to cause corresponding movement of the inner conductor along the longitudinal axis and latitudinally along the second track portion upon rotational movement of the handle member about the longitudinal axis. Proximal movement of the handle member along the longitudinal axis when the actuating member is substantially aligned with the third track portion causes corresponding proximal movement of the outer conductor and distal movement of the inner conductor such that the inner conductor is deployed relative to the outer conductor for treating tissue.

According to another embodiment of the present disclosure, a method of deploying an antenna of an ablation device includes the step of placing an introducing member relative to tissue. The introducing member is disposed on a distal end of a handle member. The method also includes the steps of advancing an antenna distally through the handle member and at least partially through the introducer and retracting the introducer within the handle member such that the antenna is at least partially deployed relative to the introducer to treat tissue.

According to another embodiment of the present disclosure, an antenna assembly includes a handle member defining a longitudinal axis and having a feedline disposed on its distal end. The feedline extends along the longitudinal axis and includes an inner conductor disposed within an outer conductor. At least a portion of the inner conductor is deployable relative to the outer conductor and is configured to deliver electrosurgical energy from an energy source to tissue. The antenna assembly also includes a first actuation member movable along a first track disposed longitudinally along at least a portion of the handle member to cause corresponding movement of the inner conductor along the longitudinal axis. The antenna assembly also includes a second actuation member movable along a second track having a latitudinal track portion and a longitudinal track portion each disposed along at least a portion of the handle member. Upon movement of the second actuation member along the latitudinal track portion into substantial alignment with the longitudinal track portion, the second actuation member is movable proximally along the longitudinal track portion to retract the outer conductor relative to the inner conductor such that at least a portion of the inner conductor is deployed relative to the outer conductor to treat tissue when the first actuation member is disposed at a distal end of the first track.

BRIEF DESCRIPTION OF THE DRAWINGS

Embodiments of the presently disclosed ablation devices are disclosed herein with reference to the drawings, wherein.

DETAILED DESCRIPTION

Figure 1:
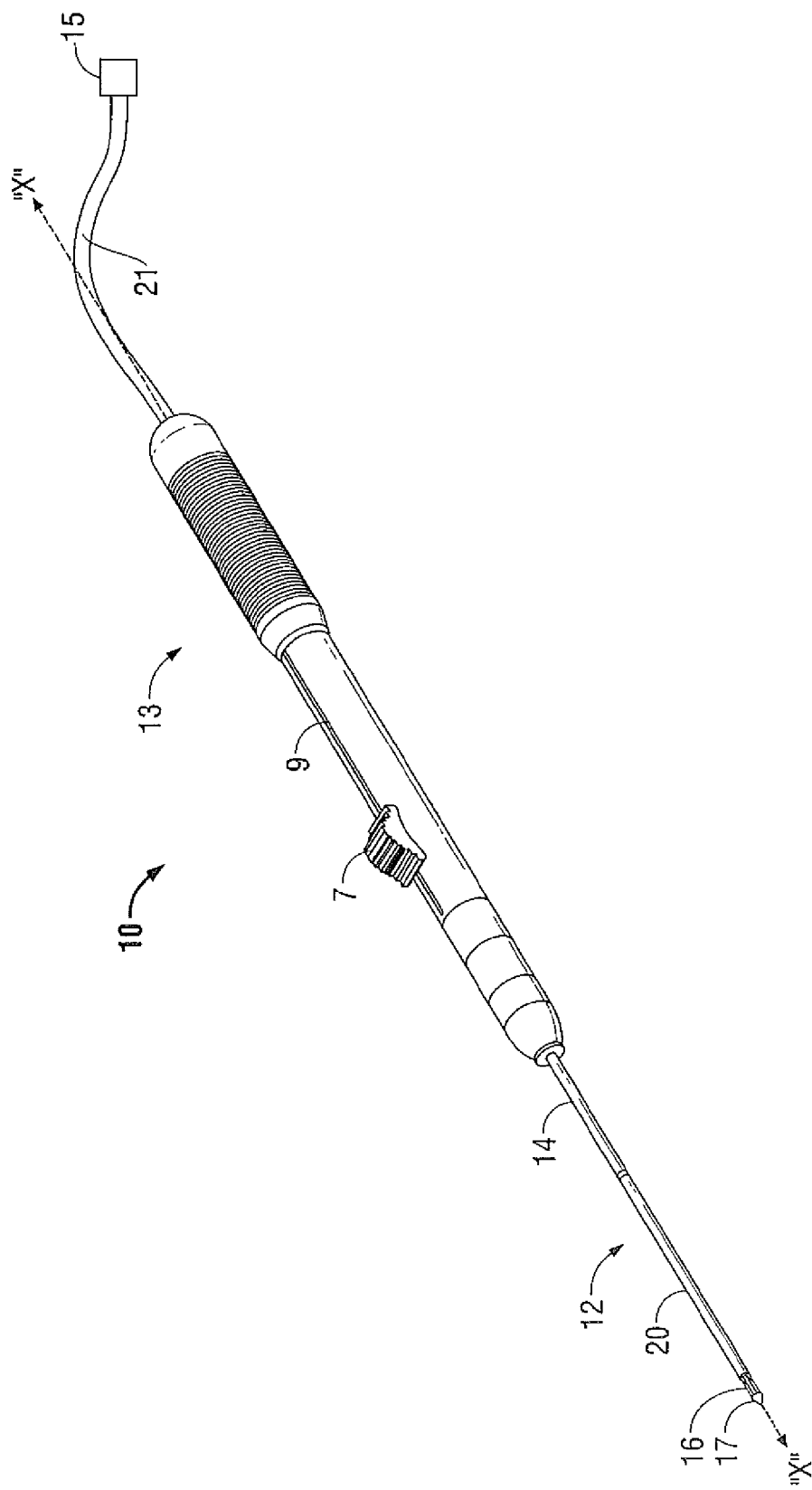
FIG. 1 is a perspective view of an ablation device in accordance with an embodiment of the present disclosure.

Embodiments of the presently disclosed microwave ablation devices are described in detail with reference to the drawings, in which like reference numerals designate identical or corresponding elements in each of the several views. As used herein the term "distal" refers to that portion of the microwave ablation device, or component thereof, farther from the user while the term "proximal" refers to that portion of the microwave ablation device or component thereof, closer to the user.

An ablation device in accordance with the present disclosure is referred to in the figures as reference numeral 10. While a microwave ablation device is described herein, it is contemplated that the present disclosure may also be used in connection with other types of ablation devices. Such ablation devices may include an antenna and/or an electrode.

Referring initially to FIG. 1, ablation device 10 includes an antenna 12 and a handle portion 13. Antenna 12 includes a shaft or feedline 14 having an inner conductor 16 and an outer conductor 20, which defines a longitudinal axis X-X. Outer conductor 20 may be, for example, an introducing structure (e.g., needle) configured to pierce and/or penetrate tissue. Ablation device 10 is connected by a cable 21 (e.g., coaxial cable) to a connector 15 that, in turn, operably connects ablation device 10 to a suitable electrosurgical generator 22 (see FIGS. 2A and 5). Additionally, an actuation element 7 is illustrated in FIG. 1 in accordance with various embodiments of the present disclosure. Actuation element 7 is operably coupled to inner conductor 16 and movable along a track 9 disposed longitudinally along at least a portion of the length of handle portion 13 to move inner conductor 16 along longitudinal axis X-X relative to outer conductor 20. More specifically, distal and proximal actuation of actuation element 7 along track 9 moves inner conductor 16 distally and proximally along longitudinal axis X-X, respectively, relative to outer conductor 20. Actuation element 7 may be, for example, a slide button, a ring, a lever, or any element ergonomically suited to be actuated along track 9.

Figure 2A:
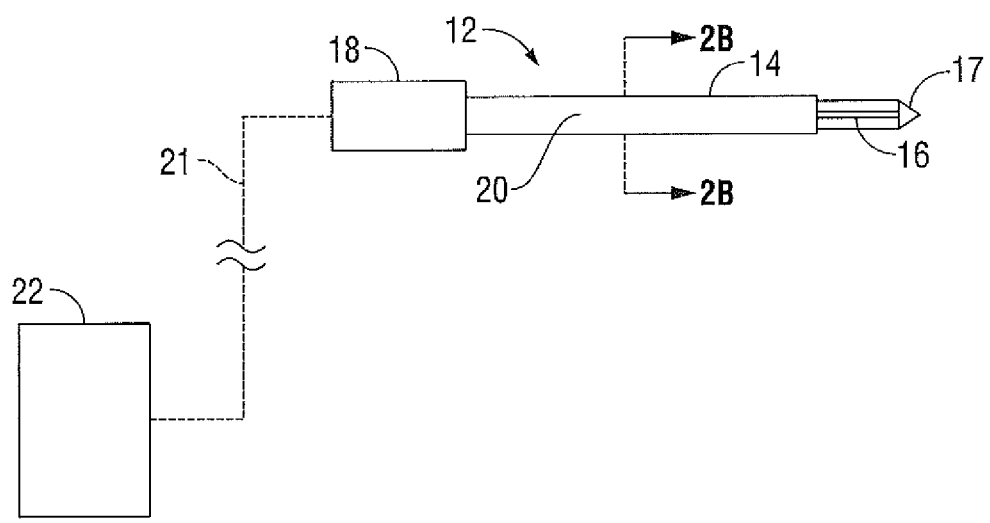
FIG. 2A is a schematic view of the ablation device of FIG. 1 connected to a generator.

As seen in FIG. 2A, inner conductor 16 includes a distal tip 17 and is extendable from outer conductor 20. Several types of inner conductor 16 may be used in connection with the disclosed ablation device 10, including an inner conductor configured to deploy substantially in line with outer conductor 20 (e.g., FIG. 2A) and an inner conductor configured to deploy in a curved orientation along a curvilinear path to define an ablation region 39 (See FIG. 5). In the illustrated embodiments of FIGS. 2A and 5, a proximal end of feedline 14 includes a coupler 18 that electrically couples antenna 12 to generator 22 via cable 21.

In some embodiments, distal tip 17 allows for insertion of antenna 12 into tissue with minimal resistance. In those cases where the antenna 12 is inserted into a pre-existing opening, distal tip 17 may be rounded or flat.

Figure 2B:
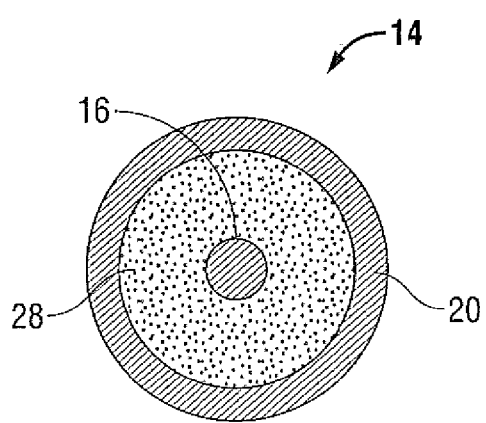
FIG. 2B is a cross-sectional view of a portion of a feedline of the ablation device of FIG. 2A taken along section line 2B-2B of FIG. 2A.

As shown in FIG. 2B, feedline 14 may be in the form of a coaxial cable. Portions of feedline 14 may be formed of outer conductor 20 surrounding inner conductor 16. Each of inner conductor 16 and/or outer conductor 20 may be made of a suitable conductive metal that may be semi-rigid or flexible, such as, for example, copper, gold, or other conductive metals with similar conductivity values. Alternatively, portions of each inner conductor 16 and outer conductor 20 may also be made from stainless steel that may additionally be plated with other materials, e.g., other conductive materials, to improve their properties, e.g., to improve conductivity or decrease energy loss, etc.

With continued reference to FIG. 2B, feedline 14 of antenna 12 is shown including a dielectric material 28 surrounding at least a portion of a length of inner conductor 16 and outer conductor 20 surrounding at least a portion of a length of dielectric material 28 and/or inner conductor 16. That is, a dielectric material 28 is interposed between inner conductor 16 and outer conductor 20, to provide insulation therebetween and is comprised of any suitable dielectric material.

In some embodiments, inner conductor 16 is configured to pierce or slice through tissue, either mechanically and/or with the aid of energy, e.g., radiofrequency or microwave. In the embodiment where inner conductor 16 mechanically pierces or slice through tissue, inner conductors 16 is thin enough to pierce or slice through tissue upon the exertion of a predetermined amount of force. Additionally or alternatively, inner conductor 16 may be configured to receive energy, e.g., from generator 22, to piece or slice through tissue or assist in piercing or slicing through tissue.

Figure 3A:
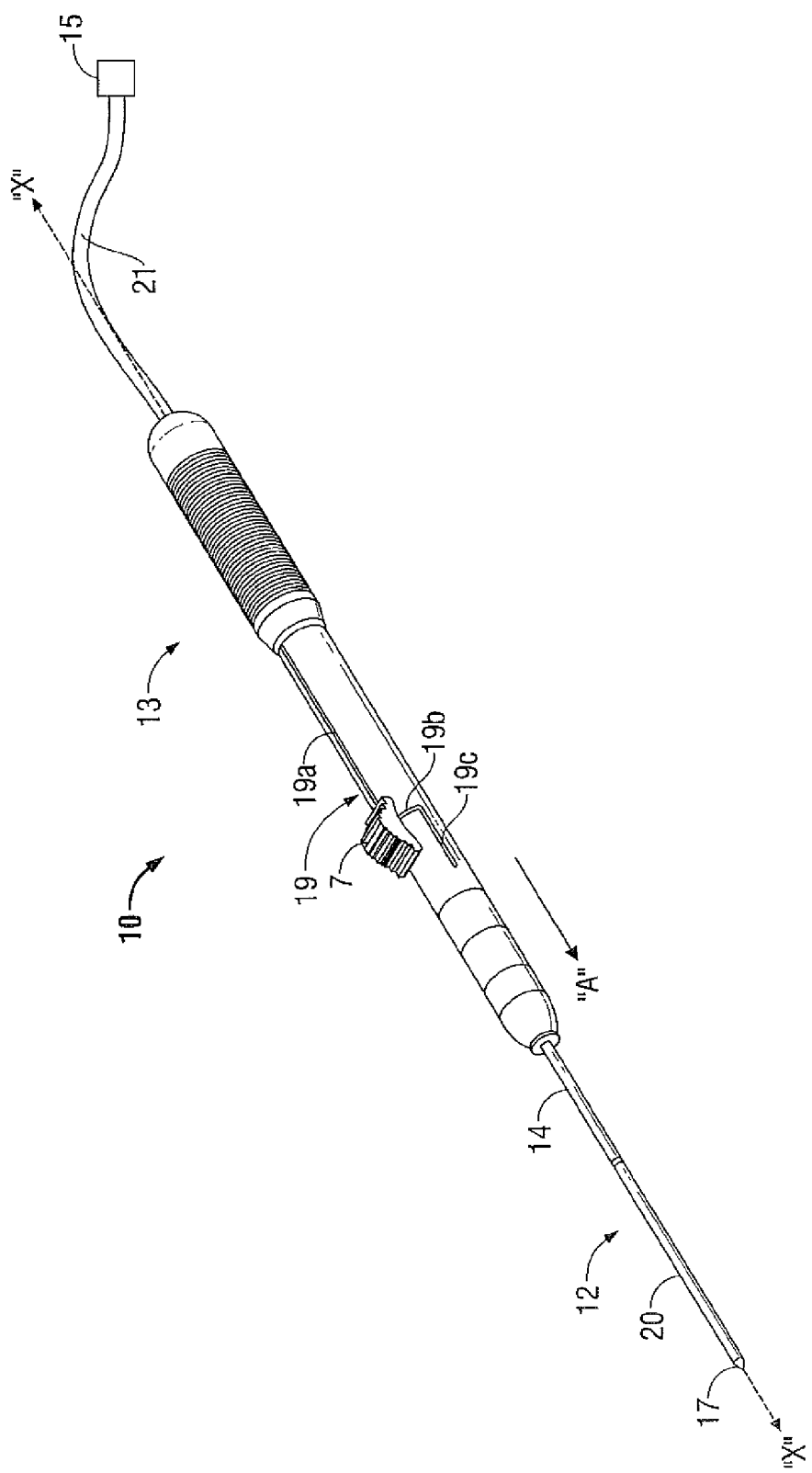
FIGS. 3A, 3B, and 3C are perspective views of an ablation device in accordance with one embodiment of the present disclosure showing sequentially the steps for deploying the radiating tip.
Figure 3B:
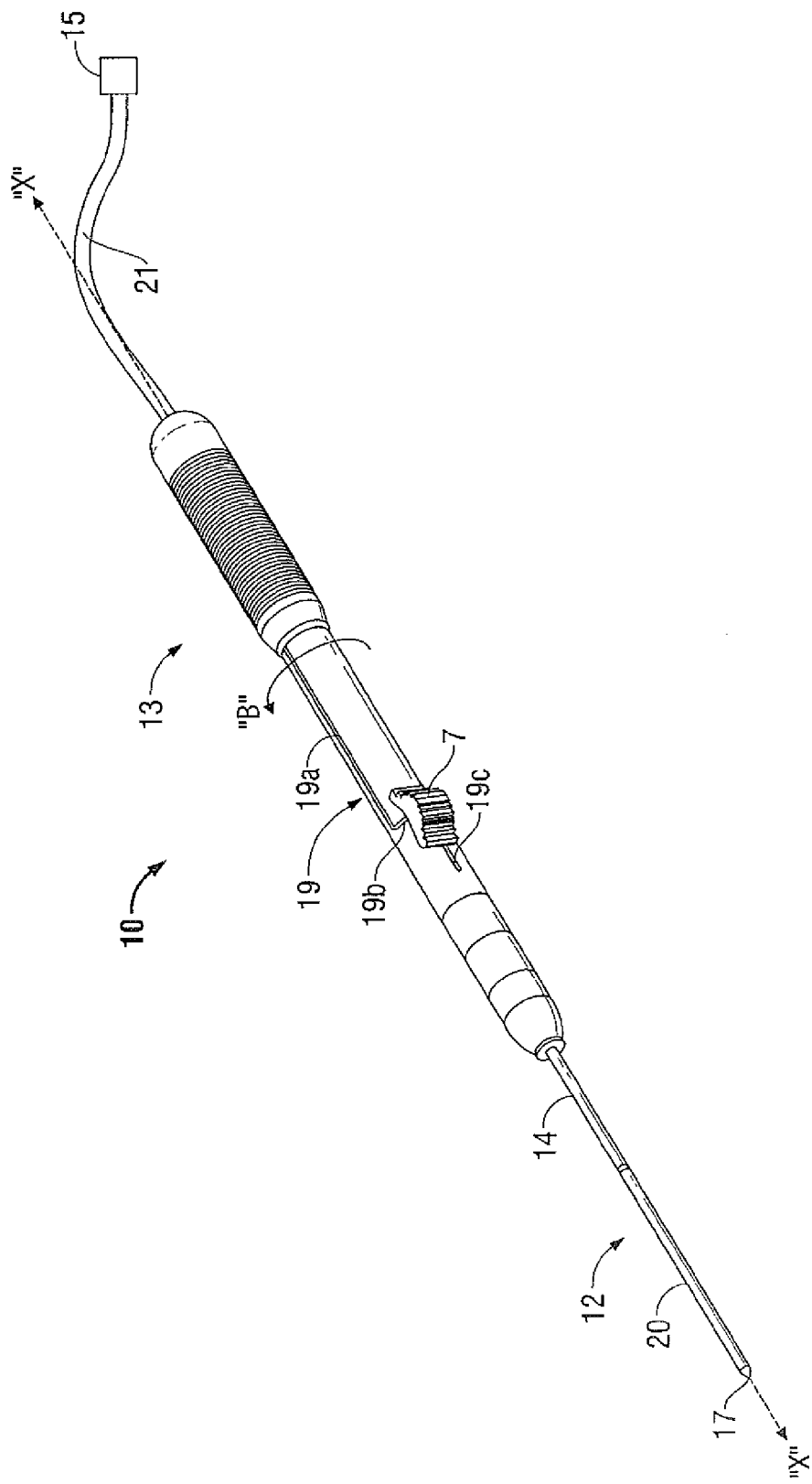
Figure 3C:
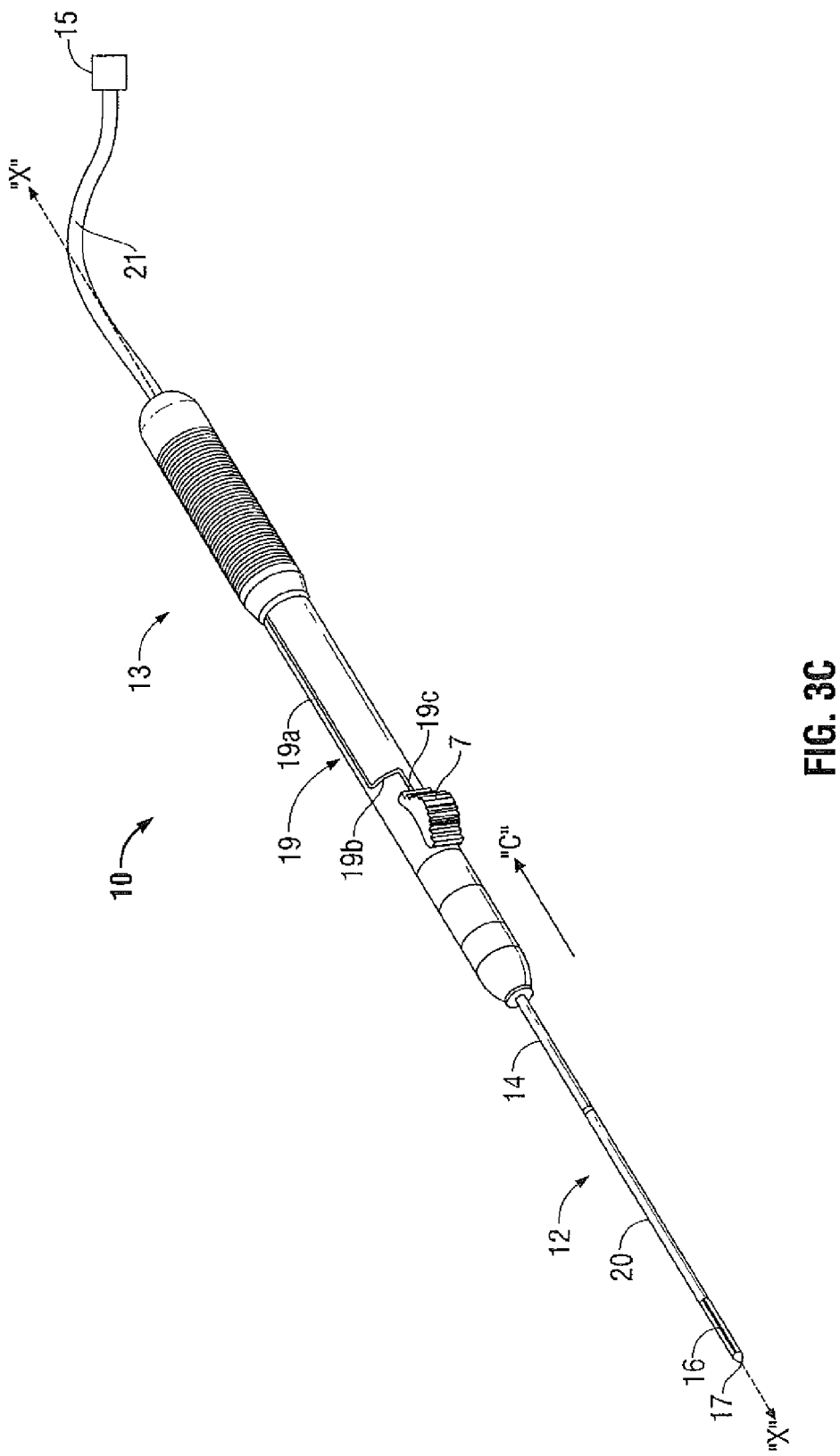

With reference to FIGS. 3A, 3B, and 3C, one embodiment of ablation device 10 includes a track 19 disposed along handle body 13 and including track portions 19a, 19b, and 19c. Track 19 operates similar to track 9 of FIG. 1 and is described below to the extent necessary to detail the differences between the embodiments. Track portions 19a and 19c are disposed longitudinally along at least a portion of the length of handle body 13 and track portion 19b is disposed between and substantially perpendicular to track portions 19a and 19c about at least a portion of the circumference of handle body 13. As substantially described above with respect to FIG. 1, actuation element 7 is operably coupled to inner conductor 16 and is movable along tracks 19a, 19b, and 19c. FIGS. 3A, 3B, and 3C illustrate distal actuation of actuation element 7 relative to handle body 13 according to one embodiment of the present disclosure. As will be discussed in further detail below, distal actuation of actuation element 7 along track portions 19a and 19c is configured to move inner conductor 16 distally along the longitudinal axis X-X. As shown in FIG. 3A, distal translation of actuation element 7 along track portion 19a, in particular, causes inner conductor 16 to move distally in the direction of directional arrow "A" such that the tip 17 of inner conductor 16 is proximate or adjacent a distal end of outer conductor 20.

As shown in FIG. 3B, rotation of handle body 13, as indicated by rotational arrow "B", causes actuation element 7 to move within track portion 19b away from track portion 19a and into substantial alignment with track portion 19c. When actuation element 7 is positioned within track portion 19b and misaligned with track portion 19a, as shown in FIG. 3B, proximal movement of actuation element 7 relative to handle body 13 is restricted. As shown in FIGS. 3B and 3C, distal movement of actuation element 7 beyond track portion 19b is permitted only when actuation element 7 is in substantial alignment with track portion 19c.

Once actuation element 7 is positioned within track portion 19b away from track portion 19a and in substantial alignment with track portion 19c (See FIG. 3B), proximal movement of handle body 13, as indicated by directional arrow "C" of FIG. 3C, causes actuation element 7 to move distally along track portion 19c. During proximal movement of handle body 13, inner conductor 16 remains stationary relative to surrounding tissue and outer conductor 20 moves proximally in translation with proximal movement of handle body 13 to retract relative to inner conductor 16, thereby exposing at least a portion of the length of inner conductor 16 to surrounding tissue.

Figure 4A:
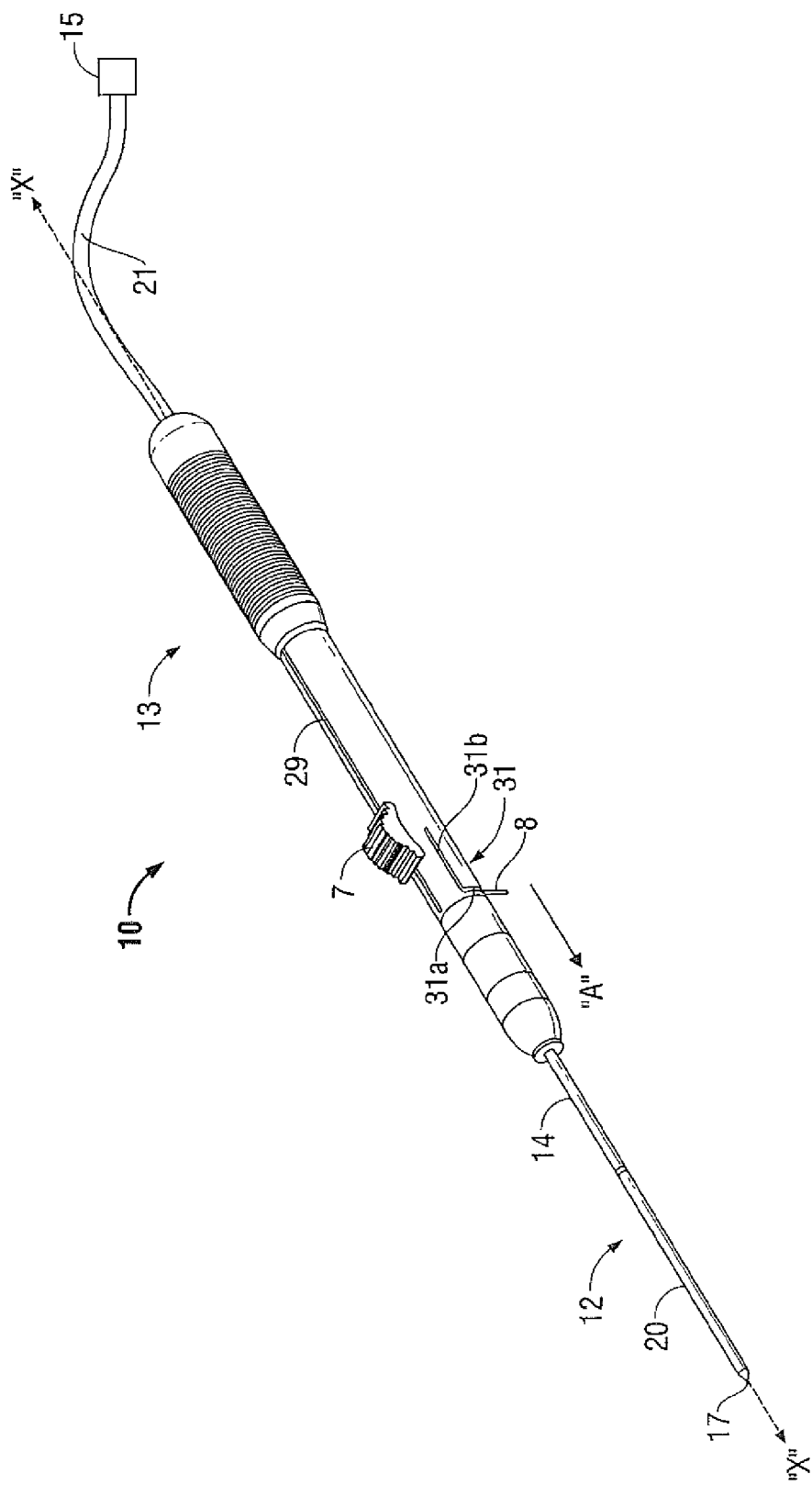
FIGS. 4A, 4B, and 4C are perspective views of an ablation device in accordance with another embodiment of the present disclosure showing sequentially the steps for deploying the radiating tip.
Figure 4B:
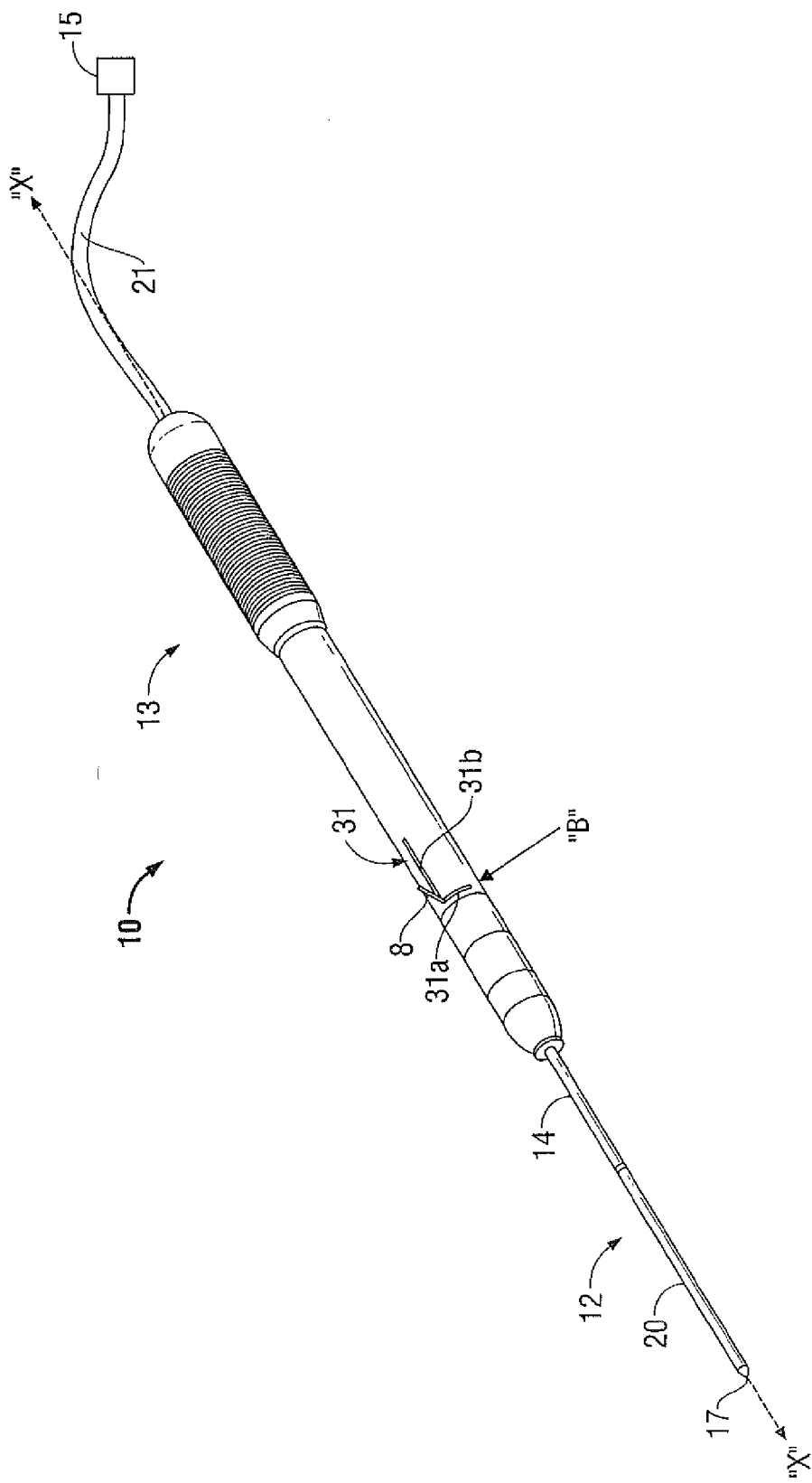
Figure 4C:
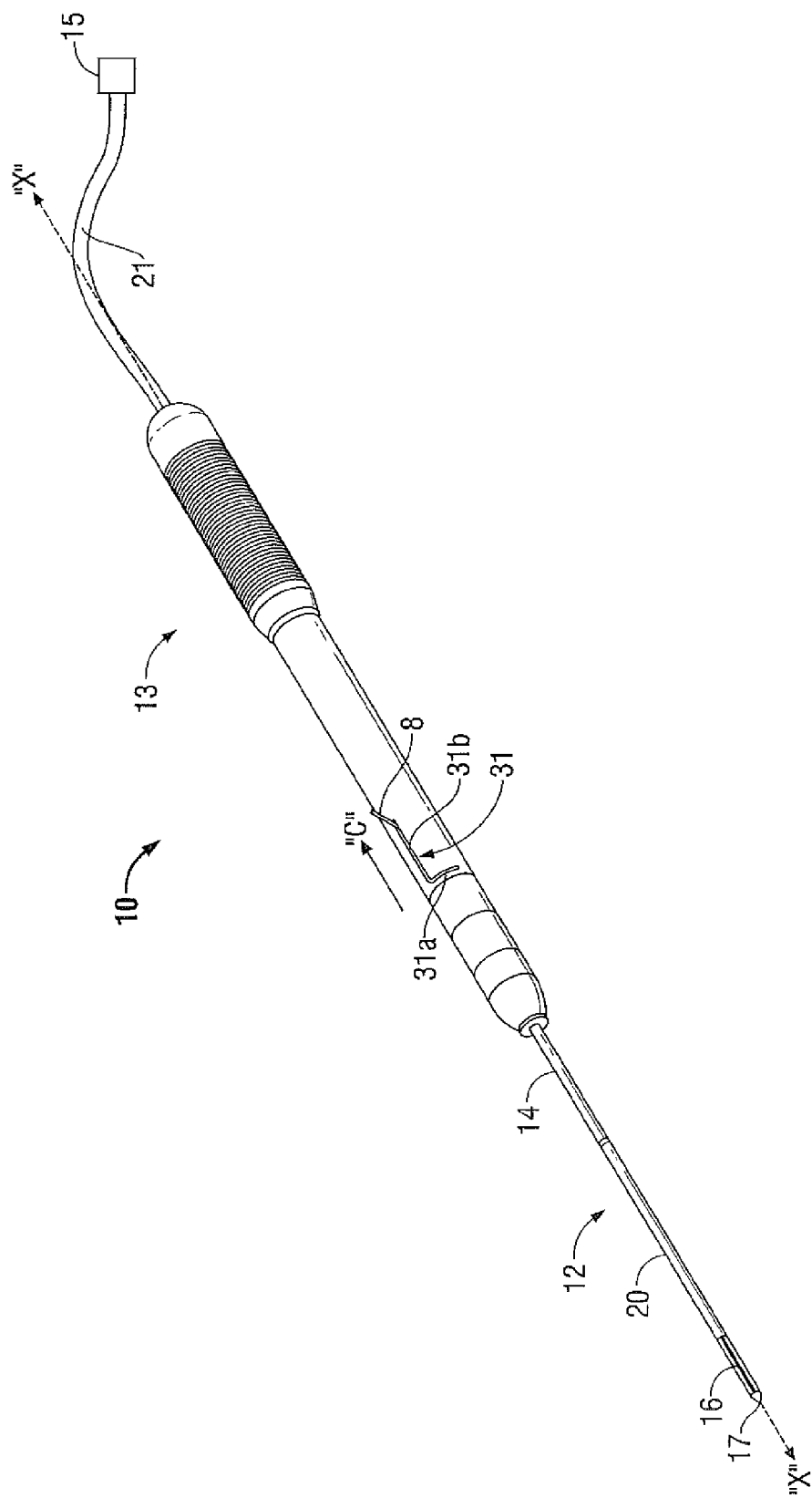

With reference to FIGS. 4A, 4B, and 4C, another embodiment of ablation device 10 includes a first track 29 and a second track 31 disposed within handle body 13. Track 29 is disposed longitudinally along at least a portion of the length of handle body 13. As substantially described above with respect to FIG. 1, actuation element 7 is operably coupled to inner conductor 16 and movable along track 29. More specifically, distal and proximal actuation of actuation element 7 along track 29 moves inner conductor 16 distally and proximally along longitudinal axis X-X, respectively, relative to outer conductor 20.

A second track 31 is disposed within handle body 13 offset an angular distance from track 29, as best shown in FIG. 4A, and includes track portions 31a and 31b. In some embodiments, track 31 may be disposed on an opposing side of handle body 13 such that track portion 31b is offset or displaced an angular distance of between about 0° and about 180° from track 29. Track portion 31a is disposed circumferentially within at least a portion of handle body 13 perpendicular to track portion 31b such that one end of track portion 31a intersects a distal end of track portion 31b. Track portion 31b extends proximally from track portion 31a longitudinally along at least a portion of the length of handle portion 13. An actuation element 8 is operably coupled to the outer conductor 20 and movable along track 31. More specifically, distal translation of actuation element 8 along track portion 31b causes outer conductor 20 to move distally in the direction of arrow "A'" (See FIG. 4A) and proximal translation of actuation element 8 along track portion 31b causes outer conductor 20 to move proximally in the direction of arrow "B'" (See FIG. 4C). Movement of actuation element 8 along track portion 31a into substantial alignment with track portion 31b (See FIG. 4B) allows subsequent proximal movement of actuation element 8 along track portion 31b, as indicated by directional arrow "C'" of FIG. 4C. This causes corresponding proximal retraction of outer conductor 20 within handle body 13 relative to inner conductor 16, thereby exposing at least a portion of inner conductor 16 to surrounding tissue.

Figure 5:
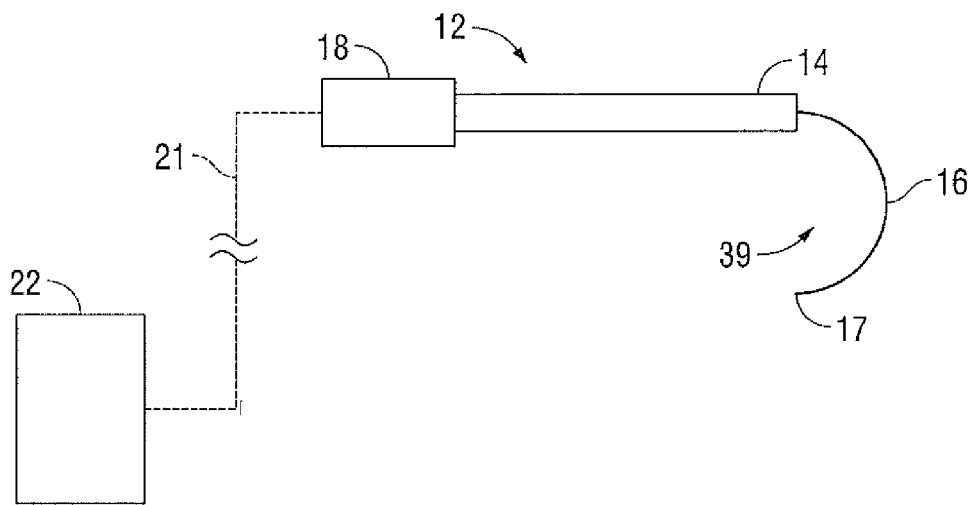
FIG. 5 is a schematic view of an ablation device connected to a generator in accordance with another embodiment of the present disclosure.

In one embodiment of ablation device 10, shown in FIG. 5, inner conductor 16 is configured to deploy in a curved orientation along a curvilinear path to define ablation region 39. More specifically, in response to the relative movement between outer conductor 20 and inner conductor 16, at least a portion of inner conductor 16 is forced radially away from longitudinal axis X-X as shown in FIG. 5. In such an embodiment, at least a portion of inner conductor 16 may be flexible.

Figure 6A:
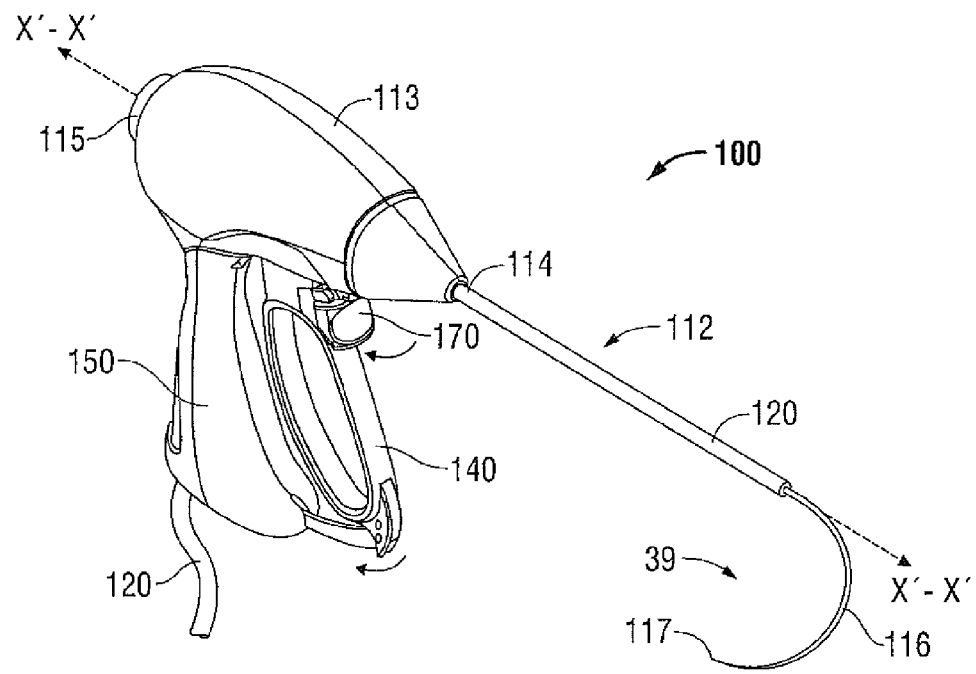
FIGS. 6A and 6B are perspective views of the ablation device of FIG. 5 according to various embodiments of the present disclosure.
Figure 6B:
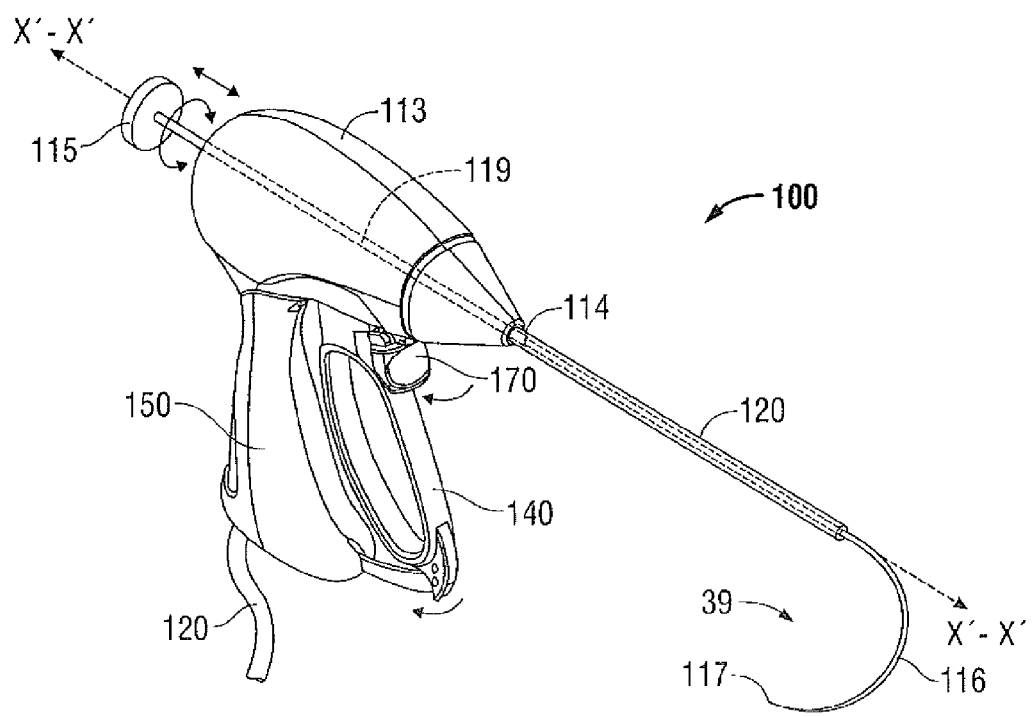

FIGS. 6A and 6B show an ablation device 100 in accordance with embodiments of the present disclosure having an inner conductor 16 configured to deploy in a curved orientation as described above with reference to FIG. 5. In particular, FIG. 6A shows an embodiment of an ablation device 100 having a handle portion 113 including a trigger assembly 170 and a movable handle 140 movable relative to a stationary handle 150. An antenna 112 is coupled to a distal end of the handle portion 113 and includes a feedline 114 having an inner conductor 116 and an outer conductor 120.

A power transmission cord 120 is shown that connects ablation device 100 to a suitable electrosurgical generator (e.g., generator 22 of FIG. 5). Trigger assembly 170 is configured to cause delivery of electromagnetic energy from the generator 22 to the inner conductor 116 via power transmission cord 120.

Movable handle 140 is operably coupled to inner conductor 116 and movable relative to stationary handle 150 to cause movement of inner conductor 116 relative to outer conductor 120. In some embodiments, movement of movable handle 140 toward stationary handle 150 advances inner conductor 116 distally relative to outer conductor 120 to expose at least a portion of the length of inner conductor 116 to surrounding tissue. In this scenario, inner conductor 116 may be incrementally advanced distally corresponding to repeated actuation of movable handle 140 relative to stationary handle 150. Alternatively or additionally, movable handle 140 may be actuated toward stationary handle 150 and held in such actuated position to cause inner conductor 116 to continually advance distally until movable handle 140 is released and/or actuated away from stationary handle 150. With this purpose in mind, ablation device 100 of FIGS. 6A and 6B includes any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that ablation device may function as intended and/or as described in embodiments disclosed herein.

In the illustrated embodiment, an optional actuation button 115 is disposed on a proximal end of handle portion 113 and is operably coupled to inner conductor 116. Substantially as described above with reference to actuation of movable handle 140 relative to stationary handle 150, actuation button 115 may be pressed repeatedly toward handle portion 113 to cause corresponding incremental distal advancement of inner conductor 116 and/or be pressed toward body portion 113 and held in such actuated position to cause corresponding continuous distal advancement of inner conductor 116.

Proximal retraction of inner conductor 116 through outer conductor 120 and within handle portion 113 may be achieved through actuation of actuation button 115 and/or actuation of movable handle 140 relative to stationary handle 150 through either of the methods described above for distally advancing inner conductor 116.

In some embodiments, actuation of movable handle 140 relative to stationary handle may be configured to cause distal movement of inner conductor 116 along the longitudinal axis X'-X' and actuation of actuation button 115 may be configured to cause proximal movement and/or retraction of inner conductor 116 along the longitudinal axis X'-X'.

As shown in FIG. 6B, actuation button 115 may be embodied as a plunger-type mechanism operably coupled to a distal end of an actuation rod 119 disposed linearly through handle portion 113 and operably coupled at a proximal end to inner conductor 116. Actuation rod 119 defines a longitudinal axis X'-X' about which actuation button 115 and actuation rod 119 may be rotated either clock-wise or counter clock-wise to effect rotation of inner conductor 116 and, thus, the location of ablation region 39 relative to surrounding tissue. Further, proximal and distal movement of actuation rod 119 along longitudinal axis X'-X' may be effected by rotation of actuation button 115 and/or actuation rod 119, pulling or pushing of actuation button 115 and/or actuation rod 119, respectively, or any combination thereof. In this scenario, the plunger-type mechanism may be configured as a linear actuator utilizing electro-mechanical components and/or hydraulic components to advance and retract inner conductor 116. With this purpose in mind and although not shown, handle portion 113 includes any suitable number of electrical connections, configurations, and/or components (e.g., resistors, capacitors, inductors, rheostats, etc.), mechanical connections, configurations, and/or components (e.g., gears, links, springs, rods, etc.), hydraulic connections, configurations, and/or components (e.g., pumps, motors, cylinders, valves, etc.), and/or electro-mechanical connections, configurations, and/or components such that ablation device may function as intended and/or as described in embodiments disclosed herein.

In some embodiments, the plunger-type configuration of actuation button 115 and actuation rod 119 may be configured to actuate in an incremental manner in response to corresponding actuation of movable handle 140 relative to stationary handle 150, for example, in substantially the same manner as a caulking gun. More specifically, inner conductor 116 may be incrementally advanced distally relative to outer conductor 120 corresponding to repeated actuation of movable handle 140 relative to stationary handle 150. Alternatively or additionally, movable handle 140 may be actuated toward stationary handle 150 and held in such actuated position to cause inner conductor 116 to continually advance distally until movable handle 140 is released and/or actuated away from stationary handle 150.

In some embodiments, actuation of movable handle 140 relative to stationary handle may be configured to cause distal movement of inner conductor 116 along the longitudinal axis X'-X' and actuation of actuation button 115 may be configured to cause proximal movement and/or retraction of inner conductor 116 along the longitudinal axis.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

What is claimed is:

1. An antenna assembly comprising:
   a handle member defining a longitudinal axis and having a feedline, the feedline extending along the longitudinal axis and including an outer conductor and an inner conductor disposed within the outer conductor, at least a portion of the inner conductor deployable relative to the outer conductor and configured to deliver energy from an energy source to tissue;
   a first track portion disposed longitudinally along at least a portion of the handle member;
   a second track portion disposed perpendicular to the first track portion and extending latitudinally along at least a portion of the handle member, a first end of the second track portion intersected by a distal end of the first track portion;
   a third track portion disposed longitudinally along at least a portion of the handle member and latitudinally offset from the first track portion, a second end of the second track portion intersected by a proximal end of the third track portion, the third track portion latitudinally offset from the second track portion; and
   an actuating member movable relative to the handle member longitudinally within the first and third track portions to cause corresponding longitudinal movement of the inner conductor along the longitudinal axis, the actuating member movable relative to the handle member latitudinally along the second track portion upon rotational movement of the handle member about the longitudinal axis, wherein proximal movement of the handle member along the longitudinal axis when the actuating member is aligned with the third track portion causes corresponding proximal movement of the outer conductor and distal movement of the inner conductor such that the inner conductor is deployed relative to the outer conductor for treating tissue.

2. The antenna assembly according to claim 1, wherein at least one of the inner conductor or the outer conductor is configured to pierce tissue.

3. The antenna assembly according to claim 1, wherein at least a portion of the inner conductor is insulated.

4. The antenna assembly according to claim 1, wherein at least a portion of the inner conductor is flexible.

5. An electrosurgical antenna assembly comprising:
   a handle;
   a feedline defining a longitudinal axis and including an outer conductor and an inner conductor, the inner conductor axially disposed within the outer conductor and configured to deliver electrosurgical energy to tissue;
   a first track portion disposed longitudinally along the handle;
   a second track portion having a first end intersected by a distal end of the first track portion;
   a third track portion disposed longitudinally along the handle and latitudinally offset from the first track portion, the third track portion having a proximal end intersecting a second end of the second track portion; and
   an actuating member movable within the first and third track portions to translate the inner conductor along the longitudinal axis relative to the outer conductor.

6. The antenna assembly according to claim 5, wherein longitudinal movement of the actuating member along the third track portion causes the inner conductor to deploy relative to the outer conductor.

7. The antenna assembly according to claim 5, wherein the first and third track portions are latitudinally offset by a length of the second track portion.

8. The antenna assembly according to claim 5, wherein the first track portion is disposed in parallel to and out of axial alignment with the third track portion.

9. The antenna assembly according to claim 5, wherein the second track portion is disposed perpendicular to the first and third track portions.

* * * * *